United States Patent [19]

Svensson

[11] 3,967,503
[45] July 6, 1976

[54] MEASURING BAND BRAKE DEVICE

[76] Inventor: Arne Bejert Svensson, Smyckegrand 14, 126 41 Hagersten, Sweden

[22] Filed: Oct. 9, 1974

[21] Appl. No.: 513,437

[52] U.S. Cl. .............................. 73/379; 188/77 W; 272/73
[51] Int. Cl.² ...................... G01L 5/02; A63B 23/04
[58] Field of Search ............... 73/379, 135; 272/73; 188/77 W; 128/2.05 R, 25 R

[56] References Cited
UNITED STATES PATENTS

| 1,580,270 | 4/1926 | Williams | 188/77 W X |
| 1,652,225 | 12/1927 | Wasson | 73/135 X |
| 3,833,216 | 9/1974 | Philbin | 272/73 |

*Primary Examiner*—James J. Gill
*Attorney, Agent, or Firm*—Sughrue, Rothwell, Mion, Zinn & Macpeak

[57] ABSTRACT

In order to attain a defined braking action, a measuring band brake device has a brake band which surrounds the brake drum through more than one turn of the same, one end of the band being free and having applied at said end a measuring force which alone decides the braking force.

2 Claims, 1 Drawing Figure

U.S. Patent   July 6, 1976   3,967,503
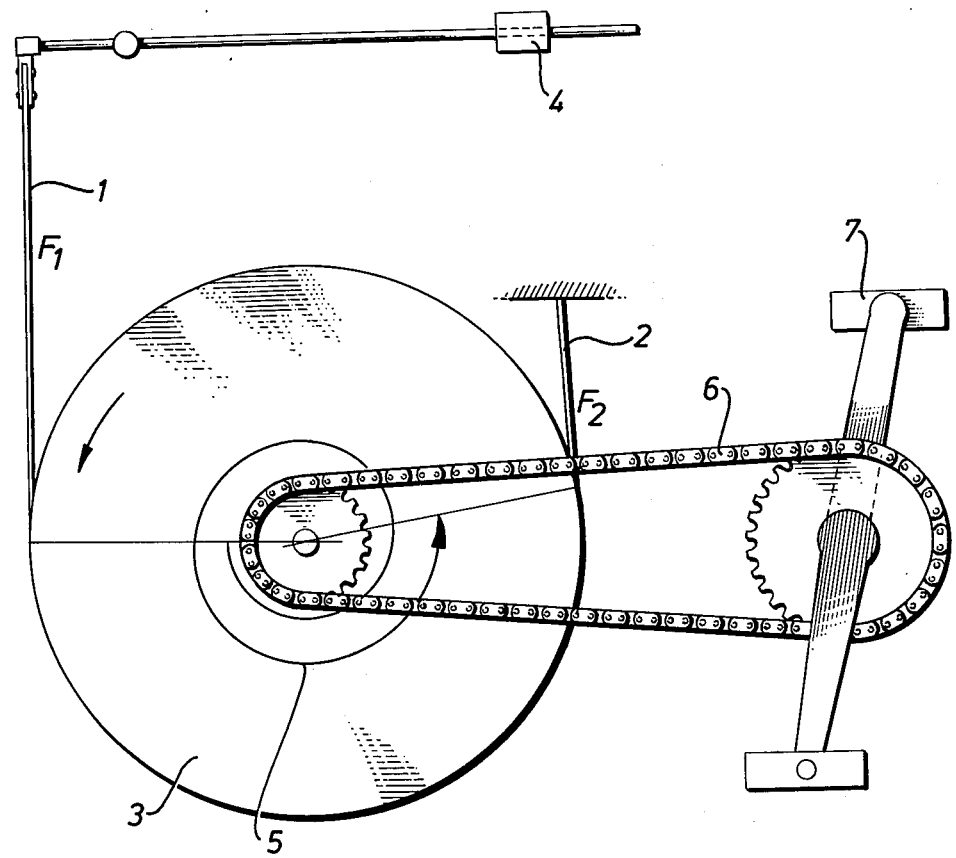

MEASURING BAND BRAKE DEVICE

To determine the braking torque in band brakes the traction forces $F_1$ and $F_2$ at the ends of the band are measured either with two balances or with one differential balance. If any influencing factor, for example the friction, is changed after applying the brake, the stresses in both band ends are changed and the application of the brake must be adjusted until the difference between the two stresses is that desired. Such band brake devices are used, for example, in so called ergometer cycles.

For use in elevators band brakes have been proposed intended to afford a safe braking action. To provide the desired braking action with the restricted space available in elevator systems, it has also been suggested, with a brake drum of restricted diameter, to wind the brake band twice around the drum.

For a similar field of application, namely for braking lifting and lowering devices for loads, it has also been proposed to decide, by means of stops arranged at both ends, a certain load value at which slipping will set in. In a modification of this prior device one stop has been replaced by a fixing means for the band.

According to the present invention which aims at solving a problem, present since a long time in ergometry with its demands for great precision and stability, of attaining a constant braking force, the braking force is fixed for each measurement by applying to one band end a force the magnitude of which alone decides the braking force by which the subject of the experiment is to be loaded.

In no prior device has the principle known in itself of providing increased braking action through a brake band which surrounds a brake drum by more than one turn, been utilized to obtain a constant braking action.

According to the invention the force at the other band end may be made neglectable by self-action (servo action), the winding or surrounding angle being chosen in such a way, that the force at said other band end becomes neglectable (either due to the fact that it becomes small as to its absolute value owing to said choice or due thereto, that said force owing to such choice is adjusted so as to compensate losses in bearings and possibly also in an existing transmission. Thereby, as already mentioned, only a single force needs to be applied and this force alone determines the braking torque.

In the accompanying drawing the measuring device according to the invention has been diagrammatically illustrated in an embodiment.

According to the same, it is conceived that the brake drum 3 of an ergometer cycle is driven through a transmission 6 from a drive wheel with pedals 7. A friction band is fixed with one end 2 in the cycle frame, is, as indicated by the angle designation 5, wound around the brake drum approximately 1.5 turns, and is with its other end 1 fixed to one arm of a pendulum balance mounted in the cycle frame, on the other arm of which balance a sliding weight 4 is movable. The stress in the band end 1 connected to the balance has been designated by $F_1$ and that in the band end 2 fixed to the frame by $F_2$.

The relationship between $F_1$ and $F_2$ is $F_1 = F_2 \cdot e^{k\phi}$ where e is the natural logarithmic base $k$ depends on the friction and $\phi$ is the angle 5 which the band takes up of the drum. By a suitable choice of k and $\phi$ $F_2$ may be made so small that it may be neglected.

The brake may be regarded as a mechanical force amplifier having an amplification of $$F_1/F_2 = G(k\phi) = e^{k\phi}.$$

The braking torque M is:

$$M = (F_1 - F_2)R = (F_1 - F_1/G(k\phi))R$$

$$M = F_1 R(1 - 1/G(k\phi))$$

where G is the gain and is a function of the Friction Coefficient K and the encircling angle $\phi$ R is the radius of the brake drum.

If the friction increases the weight is raised, the stress in the other relatively fixed end of the band decreasing so that $F_1$ will still be equally great in spite of $(Gk\phi)$ having increased. However, as long as $G(k\phi)$ is great, $1/G(k\phi)$ is neglectable beside 1, so that $F_1$ and R decide the braking torque M substantially independently of variations in the friction.

In those cases when a definite braking torque is to be taken off on a shaft, for example the crank shaft of an ergometer cycle, but the brake band is placed on the periphery of a wheel which may be driven through a transmission, power is dissipated in the transmission or bearings. In this case it is suitable to allow the factor $1/G(k\phi)$ to compensate for the said loss in the transmission. The power supplied at the pedals will then be $F_1R \, d\phi/dt$ and is thus decided entirely by $F_1$ at constant angular velocity and radius.

The advantage of the measuring brake described above is that substantial variations in friction coefficient and band length hardly influence the total braking torque.

The force $F_2$ on the input of the force amplifier adjusts itself so that the force becomes $F_1$ on the output of the amplifier. If the force $F_2$ is chosen so small that it may be neglected, even great variations in $F_2$ may be allowed for keeping $F_1$ constant. If $F_2$ is allowed to compensate for the braking forces in bearings and any transmission, $F_1$ is thus alone a direct measure of developed force which need not be corrected for possible friction losses in, for example, an ergometer cycle.

What is claimed is:

1. In a measuring band brake device intended for attaining a defined braking action, a frame, a braking drum mounted on said frame, a braking band having two ends and surrounding said drum at an encircling angle $\phi$, the improvment comprising: means for applying an outmeasuring force at one end of the braking band, the other end of the band being affixed to said frame, means allowing movement of at least one end of the braking band, and means to drive the braking drum by a human being in order to out-measure the force exerted by said human being, the braking band surrounding the brake drum through more than one turn of the drum at an encircling angle $\phi$ at which the force at the affixed end of the band is negligible thus enabling the force exerted by the human being to be defined solely by the outmeasuring force applied at one end of the braking band.

2. A device according to claim 1, in which the force at said affixed band end, by choice of the angle $\phi$, is adjustable to compensate for transmission losses by movement of point of affixation.

* * * * *